United States Patent [19]

Sandman

[11] 4,355,632
[45] Oct. 26, 1982

[54] ANTI-SHOCK PRESSURE GARMENT

[75] Inventor: Terry L. Sandman, Toledo, Ohio

[73] Assignee: Jobst Institute, Inc., Toledo, Ohio

[21] Appl. No.: 175,733

[22] Filed: Aug. 6, 1980

[51] Int. Cl.³ .............................................. A61H 1/00
[52] U.S. Cl. .................................................. 128/24 R
[58] Field of Search ............... 128/24, 24.2, DIG. 20, 128/38–40, 60, 64; 2/269, DIG. 7

[56] References Cited

U.S. PATENT DOCUMENTS

| | | | |
|---|---|---|---|
| 1,608,239 | 11/1926 | Rosett | 128/64 |
| 3,933,150 | 1/1976 | Kaplan | 128/DIG. 20 |
| 3,982,531 | 9/1976 | Schaffer | 128/DIG. 20 |
| 4,091,804 | 5/1978 | Hasty | 128/24 R |
| 4,120,297 | 10/1978 | Rabischong | 128/DIG. 20 |
| 4,149,275 | 4/1979 | Sanchez | 2/269 |

Primary Examiner—Richard C. Pinkham
Assistant Examiner—Carl Moy
Attorney, Agent, or Firm—Wilson, Fraser, Barker & Clemens

[57] ABSTRACT

An anti-shock pressure garment having a trouser portion and an upper portion connected thereto forming a one-piece construction. The upper portion has a flexible back panel which is not inflatable and a front panel containing a plurality of pressure chambers or bladders which wherein inflated inpose pressure on the thorax and abdomen of the patient. The legs of the trousers have pressure chambers or bladders which when wrapped about the patient's legs, can impose the desired pressure. The upper portion is length adjustable to allow the garment to cover a greater size range of patients. This is accomplished by folding down the upper portion of the front and rear panels and securing them in folded position.

5 Claims, 5 Drawing Figures

ANTI-SHOCK PRESSURE GARMENT

BACKGROUND OF THE INVENTION

The emergency treatment of persons suffering from shock, effort must be made to overcome a state of circulatory collapse where insufficient return of blood to the heart takes place. In such instances, the venous system becomes dilated permitting blood to pool and, as a result, stagnation and clotting take place. Compensatory means must be provided to cause the return of sufficient blood to the heart.

In an attempt to cope with this problem, inflatable garments have been developed in the form of trousers, for example, to which pressure fluid is introduced to a bladder for inflating the same and applying pressure to the patient's legs to decrease the volume of blood trapped or pooled in that region. In a similar manner, pressure has been applied to the abdominal region. Garments for use in applying abdominal pressure heretofore failed to use to afford adequate length for the assured treatment of ruptured abdominal aortic aneurysm occurring in patients of above average, and in some instances, average height.

The prior art U.S. Pat. Nos. 4,039,039 to Gottfried and 3,933,150 to Kaplan et al are illustrative of pressure applying garments. The devices shown in these patents do not afford pressurizing means for the thorax and insufficient means with respect to the abdomen. No arrangement is present in these devices for accommodating persons of different heights.

SUMMARY OF THE INVENTION

In accordance with the present invention, a garment is produced having trouser legs provided with bladders, which are inflatable after being wrapped around a patient's legs and secured in place by separable fastener devices. In this manner, pressure is imposed upon the patient's leg to thereby decrease the volume of venous blood which may be pooled in those areas. Connected to the flexible fabric material of the trouser legs of the garment in the crotch region is an upper garment which has a non-inflatable back panel and an inflatable front panel having bladder means for covering the complete abdominal area and also the thorax. The bladder means may typically consist of several bladders, either independent of each other, or in communication with each other, as by pressure sensitive valves. Structure is such that link adjustment can be effected, thus assuring usefulness of the garment in treating patients of a greater size range than has been possible with prior art structure. The upper portion of the back panel can be folded rearwardly upon itself and secured, and the upper portion of the front bladder containing panel can be folded forwardly upon itself and secured. The upper garment thus can be readily increased or decreased in size in order to accommodate the particular patient's requirements.

BRIEF DESCRIPTION OF THE DRAWINGS

Other objects and advantages of the invention will become readily apparent to those skilled in the art from reading the following detailed description of a preferred embodiment of the invention when considered in the light of the accompanying claims, in which:

DETAILED DESCRIPTION OF THE PREFERRED EMBODIMENT

Figure 1:
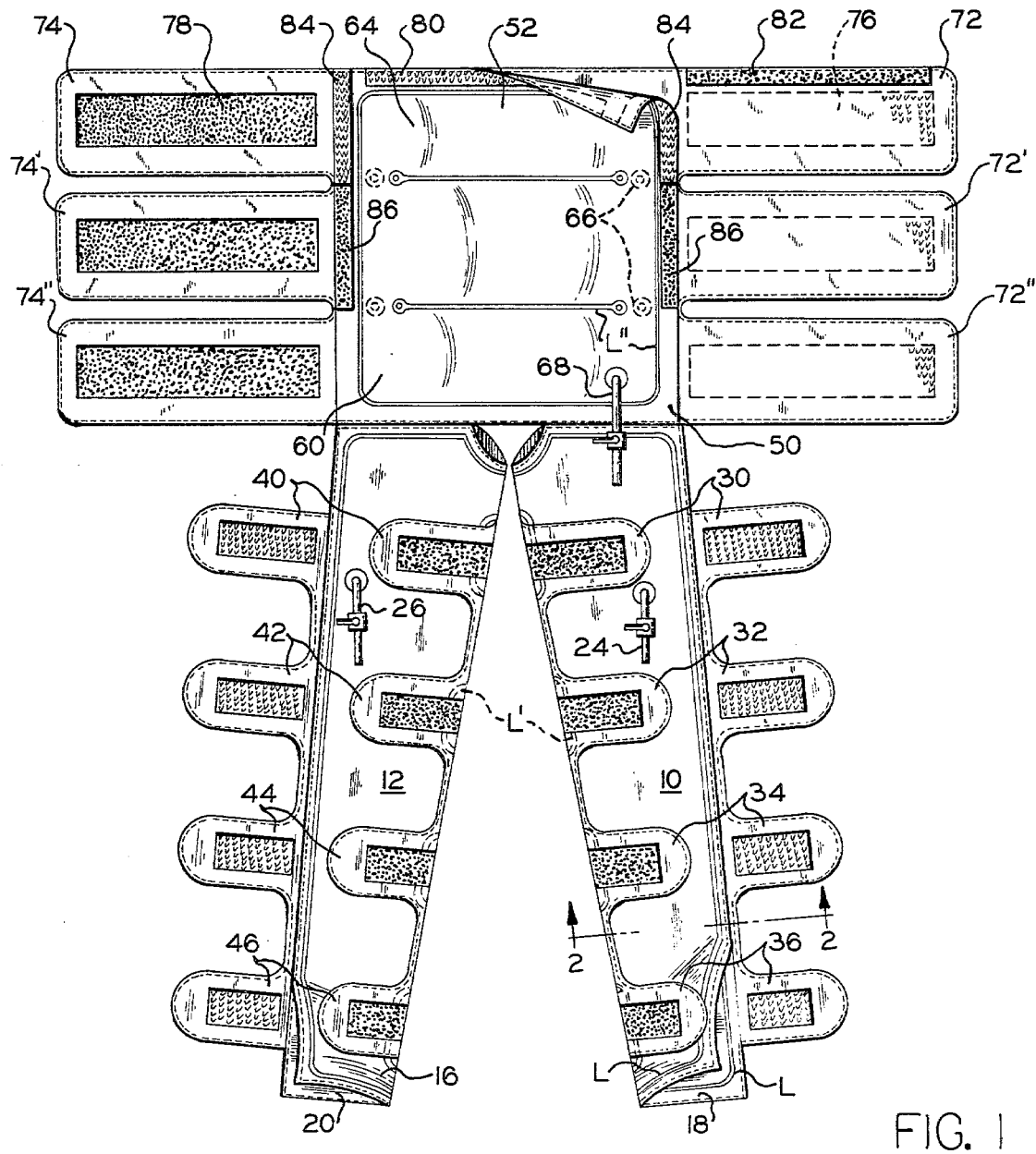
FIG. 1 is a top plan view of a pressure garment in open position and embodying the novel features of the invention.

The illustrated embodiment of the invention comprises a pair of longitudinally folded trouser leg sections 10 and 12 having outer panels 14 and 16 integral with inner panels 18 and 20, respectively. The outer panels 14, 16 and the inner panels 18, 20 of the trouser leg sections 10 and 12 are typically fabricated from a woven fabric F having a gas impermeable coating C on one surface thereof. It has been found that satisfactory results may be achieved by employing a taffeta fabric of nylon having a thin layer of a polyurethane plastic formed on one surface thereof. It will be appreciated that while the polyurethane coating C imparts gas impervious characteristics to the fabric F, it is also inherently light in weight, flexible, and can be readily sealed or joined to a mating layer of similar plastic upon the application of heat and pressure. The free edges of the cooperating outer and inner panels are typically sealed to form definable inflatable chambers or bladders therebetween. Since each of the trouser leg sections 10 and 12 is formed in a similar fashion, specific explanation of the formation of inflatable chambers or bladders will be made only in respect of the trouser leg section 10. As explained herein above, the trouser leg section 10 includes an outer panel 14 and an associated inner panel 18. These panels superimpose on one another in a manner such that the polyurethane coatings are enfacing juxtaposed relation. Then the free edges of the outer panel 14 and the inner panel 18 are joined together by appropriate sealing means such as for example an electronic welding system which causes the polyurethane coating to be selectively heated to a thermoplastic state along a relatively narrow line, generally indicated by reference L on the drawings, and with the simultaneous application of pressure, the juxtaposed polyurethane coating C will be joined together to form a gas-tight seal. In a similar manner, the inner or inseam portion of the cooperating panel 14 and inner panel 18 of the trouser leg section 10 are joined together along a narrow line, generally indicated by reference L' on the drawing. The line L' will be noted as being discontinuous, thereby forming spaced-apart passageway to permit communication between the rather discrete bladder formed in the outer panel 14 and the inner panel 18.

Inflation of the bladder of each of the trouser leg sections 10 and 12 is achieved through a valve controlled gas pressure connection 24 for the trouser leg section 10 and a similar connection 26 for the trouser leg section 12. Each connection is typically provided with a manually controlled valve operable to contain pressure fluid within the interior of the respective bladder.

In use, after the legs of the patient are positioned in the appropriate trouser leg section, they are secured snuggly by oppositely disposed pairs of securing straps 30, 32, 34, and 36 for the leg section 10; and 40, 42, 44, and 46 for the leg section 12. The pairs of straps are typically releasably secured together by the Velcro type fastening strips which include two cooperating materials, usually referred to as a hook portion and a loop portion. One strap of each pair is provided with a hook portion and the other cooperating strap with a loop portion, so that upon applying one to the other, a secure fastener is readily obtained without exerting pressure against the patient's body or injury. The hook and loop fasteners employed are preferably color coded to facilitate correct assembly of the garment, even under poor light conditions.

The upper portion of the trouser leg sections 10 and 12 is secured in any suitable manner to an upper garment section 50 to cover the abdominal and thorax body areas and to insure their proper location. The front trouser leg panels 14 and 16 are secured to an upper front panel 52 substantially coextensive with the width dimension of the trouser leg section. The panel 52 is formed of two substantially rectangular panels of nylon taffeta fabric having a polyurethane coating with the side edges sealed together in the same manner as described with respect to the trouser leg sections 10 and 12 to provide inflatable chambers or bladders in ascending order 60, 62 and 64. Between each of the adjacent bladders is an integral sealing line L" which effectively joins the two layers of bladder material. These separate adjacent bladders are either completely closed so that pressure fluid can pass to one from another through pressure sensitive valve 66, for example, or partially sealed to enable pressure fluid to flow from one bladder to another in a partially restricted manner. The valve 66 may typically be of the type which will allow pressure fluid to pass therethrough only upon being exposed to a predetermined pressure. A valve controlled pressure connection 68 provided with a manually controlled valve enables pressure fluid, such as air or other gases including refrigerant gases or fluids such as water, to be introduced to effect the desired inflation.

The upper panel 52 of the garment has an uninflatable rear panel 70 of approximately the same planar dimensions as the front panel 52 and is secured at its lower edge to the upper edge of the inner trouser panels 18 and 20. On opposite sides of the rear panel 70 are laterally extending securing flaps 72, 72', and 72" on the right side and corresponding cooperating flaps 74, 74', and 74" on the left side. The corresponding flaps have hook and loop fastening strips 76 and 78, respectively. A strip 80 on the upper marginal edge of the upper bladder 64 can be engaged by a strip 82 on the uppermost flap 72 in the above hook and loop fastening procedure for securing these parts together, and thereby, will effectively maintain the upper panel in the desired position when in use, as will become readily manifest hereinafter.

Figure 4:
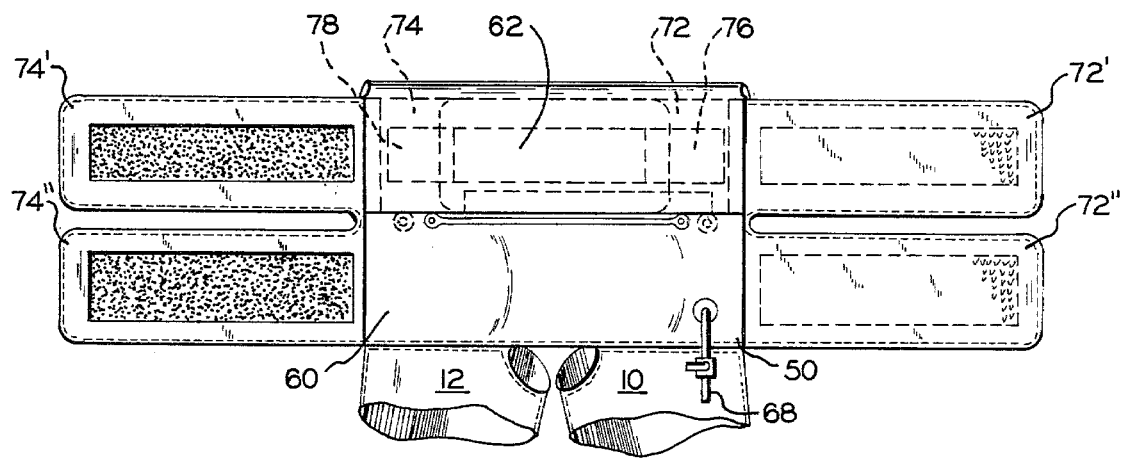
FIG. 4 is similar to FIG. 3 of the upper portion of the garment and shows the turned-down upper bladder section for the purpose of shortening the effective length of the associated garment.

A feature of this invention resides in enabling the upper bladder 64 of the panel 52 to be folded forwardly and downwardly upon the next lower bladder 62 to effectively shorten the overall length of the garment, as shown in FIG. 4. In this connection, it should be explained that former garments did not afford adequate abdominal section length for the proper treatment of ruptured aortic aneurysm occurring in a patient of above average height. As indicated, the garment may be extended to a height sufficient to cover the patient's thorax, as well as the abdominal region. Thus, this adjustment enables the garment to cover a greater size range of patients in the treatment of persons above and below average height, the obese, the women in later stages of pregnancy.

For reducing the height of the garment, the upper bladder portion 64 of the upper panel 52 can be folded forwardly and downwardly upon bladder section 62. For holding the bladder section 64 in the downwardly folded position are hook and loop fastening strips 84 and 86 on the respective marginal side edges of the bladder portions 64 and 62. At this time, the sealing flaps 72 and 74 extending outwardly in opposite directions from the upper portion of the back panel 70 are flexed into engagement and retained in place by the hook and loop engagement of the respective fastening strip 76 and 78. Finally, the upper portion of the back panel 70 along with the sealing flaps 72 and 74 are unitarily folded rearwardly and downwardly upon the rear portion of the back panel and held in such folded position by Velcro type fastening strips not shown.

Figure 5:
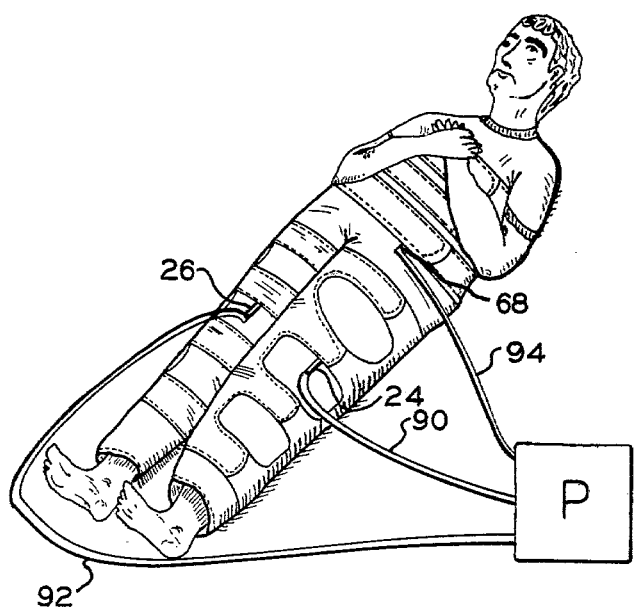
FIG. 5 is a perspective view of the garment illustrated in FIGS. 1, 2, 3, and 4 enclosing a patient and schematically illustrating a pressurizing system.
Figure 2:
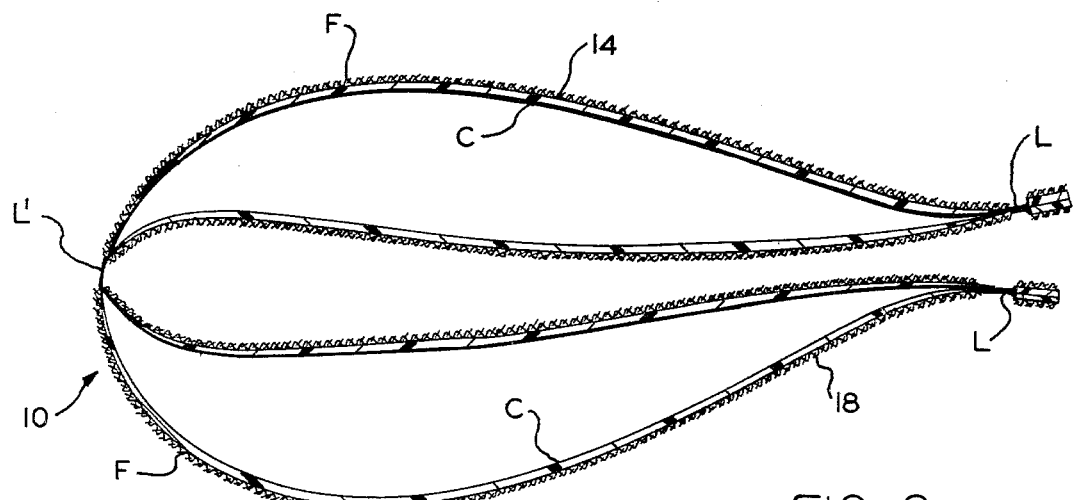
FIG. 2 is a sectional view taken along line 22 of FIG. 1.
Figure 3:
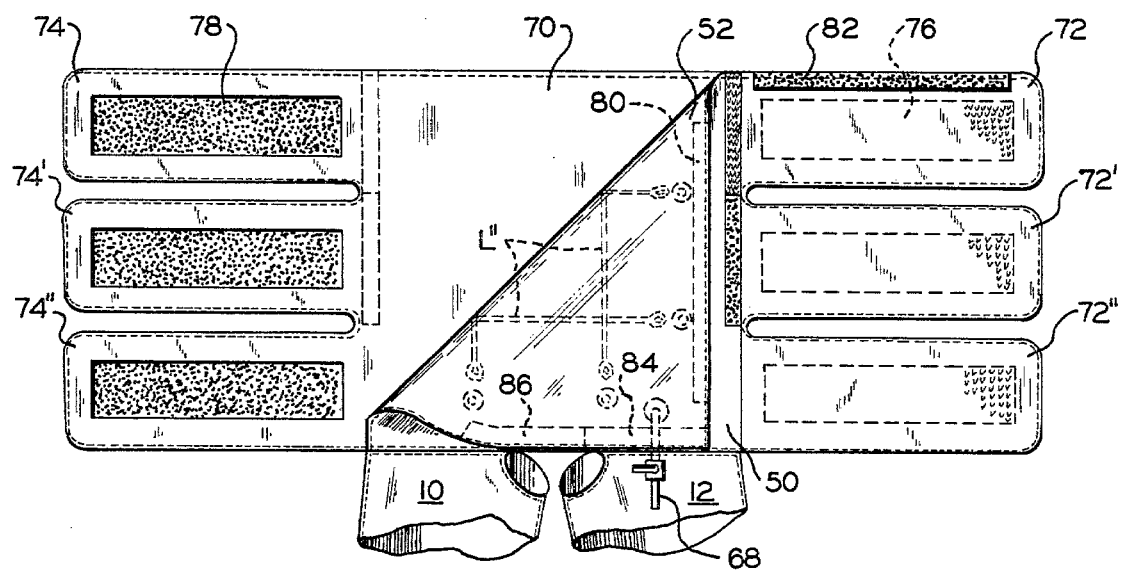
FIG. 3 is an enlarged fragmentary plan view illustrating the upper portion of the garment illustrated in FIG. 1 with the front inflatable end portion being folded back to show the rear panel and associated sealing flap.

In use, the pressure fluid connections 24 and 26 of the trouser leg sections 10 and 12, respectively may receive pressure fluid, such as air under pressure, through suitable conduits 90 and 92, which are coupled to a source of pressure fluid such as a Pump, as illustrated in FIG. 5. The pressure fluid connection 68 may be coupled to the pump P by a conduit 94 in the same manner as the pressure connections 24 and 26. Manifestly, the amount of inflation of the respective bladder portions of the garment may be controlled by suitable controlled (not shown) which would be employed for safety purposes. It will be understood that after the desired pressure is achieved within the respective bladders, the manually controlled valve of the pressure connections 24, 26, and 68 are closed. Further, mechanically actuated valves may be employed to trigger bladder inflation or sections thereof at either predetermined or selectable pressure ranges or predetermined or selectable time ranges. Such valves may also be utilized to inflate one or more sections to different pressures than other sections; or may be used sequentially to inflate and/or deflate one or more sections.

Although I have shown and described as a preferred embodiment the best form of the invention known at this time, it is to be understood that changes in construction, arrangement, and choice of materials may be effected without departing from the invention.

What is claimed is:

1. An anti-shock pressure garment to cover the thorax and abdominal regions of a patient comprising:
    (a) a rear flexible panel for flatwise application to the back of the patient;
    (b) an inflatable front flexible panel for covering and imposing pressure on the patient's thorax and abdomen; said inflatable front panel including a plurality of horizontally disposed inflatable bladders providing vertically spaced individual sections, the uppermost section being foldable downwardly and forwardly upon itself for height adjustment, means holding said section in folded position, and means for connecting said sections to a source of pressure fluid; and
    (c) fastener means for securing and maintaining said panels in operative position.

2. A garment as defined in claim 1 wherein said fastener means comprises corresponding flaps on opposite sides of said rear panel adopted to embrace the said front panel in overlapping relation; and hook and loop fasteners on said flaps, respectively, for securing same in place; and said fastener means for holding said folded down front panel section includes hook and loop fasteners on said section and the adjacent portion of said front panel, respectively.

3. A garment as defined in claim 1 wherein the vertically spaced sections of said front panel are independently inflatable.

4. A garment as defined in claim 3 including pressure sensitive valve means between adjacent sections whereby pressure fluid will pass from one section to another section when the pressure in said one section exceeds a predetermined pressure.

5. An anti-shock pressure garment to cover the thorax and abdominal regions of a patient, comprising:
   (a) a separate rear panel for flatwise application to the back of a patient;
   (b) a separate front panel for covering the patient's thorax and abdomen;
   (c) a plurality of horizontal bladder portions formed in said front panel adapted to be inflated for imposing pressure;
   (d) a series of lateral flaps on side edges of said rear panel adapted to fold overlappingly on said front panel;
   (e) hook and loop fasteners on said flaps for securing said front flaps in operative position;
   (f) means enabling the uppermost of horizontal bladder portions of said front panel to be folded forwardly and downwardly upon the next adjacent one of said bladder portion;
   (g) fastener means in the form of hook and loop fasteners to secure said folded portions to the adjacent bladder portions;
   (h) means for enabling a portion of said rear panel to be folded rearwardly and downwardly;
   (i) means for securing said folded down portion of said rear panel in place;
   (j) a trouser portion having legs secured to said front and rear panels at the lower edges thereof, each of said trouser legs having inflatable bladders for imposing pressure on a patient's legs after being wrapped around the same;
   (k) hook and loop fasteners for securing each of said trouser legs in folded position; and means for introducing pressure fluid to said bladders for generating the desired pressure against the patient's body.

* * * * *